US00PP08305P

United States Patent [19]

Schumann

[11] Patent Number: Plant 8,305

[45] Date of Patent: Jul. 13, 1993

[54] GERANIUM PLANT NAMED FISLU

[75] Inventor: Ingeborg Schumann, Münster, Fed. Rep. of Germany

[73] Assignee: Florfis AG, Binningen, Switzerland

[21] Appl. No.: 779,295

[22] Filed: Oct. 18, 1991

[51] Int. Cl.[5] ..... A01H 5/00

[52] U.S. Cl. ..... Plt./87.12

[58] Field of Search ..... Plt./87.12

*Primary Examiner*—James R. Feyrer

[57] ABSTRACT

A new and distinct cultivar of geranium named Fislu, particularly characterized by the combined features of red purple flower color, double flower form, relatively dark foliage without zonation, medium to vigorous growth and well branch, bushy plant habit, late flower response, and good rooting ability.

1 Drawing Sheet

The present invention comprises a new and distinct cultivar of geranium, botanically known as *Pelargonium peltatum L'Hert,* and hereinafter referred to by the cultivar anmed FISLU.

Fislu is a product of planned breeding program which had the objective of creating new geranium cultivars with purple flower color, double flower form, good branching and fast rooting characteristics.

Fislu was originated from a hybridization made by the inventor Ingeborg Schumann in a controlled breeding program in Galdar, Gran Canaria, Spain in 1985. The female parent was a hybrid resulting from a cross of Italian Gem and El Gaucho. Italian Gem is characterized by pink violet flower color and dark green leaves, El Gaucho by salmon pink semi-double flowers. The male parent of Fislu was Martine, having bright red single flowers and vigorous growth.

Fislu was discovered and selected as one flowering plant within the progeny of the stated cross by the inventor in spring 1985 in a controlled environment in Hillscheid, Federal Republic of Germany.

The first act of asexual reproduction of Fislu was accomplished when vegetative cuttings were taken from the initial selection in May 1986 in a controlled environment in Galdar, Gran Canaria, Spain, by, or under the supervision of, Ingeborg Schumann.

Horticultural examination of rooted cuttings initiated in 1987 and continuing thereafter has demonstrated that the combination of characteristics as herein disclosed for Fislu are firmly fixed and are retained through successive generations of asexual reproduction.

Fislu has not been observed under all possible environmental conditions. The phenotype may vary somewhat with variations in environment such as temperature, light intensity and day length, without, however, any variance in the genotype. The following observations measurements, and comparisons describe plants grown in Hillscheid, Federal Republic of Germany under greenhouse conditions which approximate those generally used in commercial practice.

The following traits have been repeatedly observed and are determined to be basic characteristics of Fislu, which in combination distinguish this geranium as a new and distinct cultivar:

1. Red-purple flower color
2. Double flower form
3. Late flowering, but rich flower production during the summer 4. Comparatively dark green foliage without zonation
5. Medium growth habit
6. Very good branching characteristics
7. Fast rooting The accompanying color photographic drawing is a side elevational view showing typical flower and foliage characteristics of Fislu, with colors being as true as possible with illustrations of this type.

In the following description color references are made to The Royal Horticultural Society Color Chart. The color values were determined indoors from flowers taken from plants grown outdoors in June at Hillscheid, Federal Republic of Germany.

Classification:

*Botanical.*—A hybrid of the species *Pelargonium peltatum L'Hert.*

*Commercial.*—Ivy geranium, cv. Fislu.

INFLORESCENCE

A. Umbel:

*Average diameter.*—89 mm.

*Average depth.*—49 mm.

*Peduncle length.*—130 mm.

*Pedicel length.*—30 mm.

*Pedicel color.*—Partly anthocyanin colored.

*Number of flowers per umbel.*—7.7.

B. Corolla:

*Average diameter.*—45 mm.

*Form.*—Double.

*Number of petals.*—16–17.

*Color (general tonality from a distance of three meters).*—Red purple.

*Color of upper surface.*—R.H.S. 66A.

*Color of lower side of petals.*—Light purple to white, marbeled with dark purple veins.

*Number of sepals.*—5–6.

*Color of sepals.*—Green, partly anthocyanin colored.

*Petaloids.*—There is average of two or three small petals with a stamen on top; petaloids are essentially transformed anthers.

C. Bud:

*Shape.*—Elongated.

*Color (sepals).*—Green.

*Color (tips of petals).*—Light purple to pink, marbled.

D. Reproductive organs:

*Androecium.*—3–5 anthers (2–3 fertile), and white filament, mature stamen with orange pollen, and violet to black lower side.

Gynoecium.—5–6 lobed stigma, white filament, dark red to violet stigma.

E. Spring flowering response period: In Hillscheid, Federal Republic of Germany, in 1989 20% of plants with at least 1 flower opened 11 weeks after planting of unrooted cuttings.

F. Outdoor flower production: The flower count in 1989 in Hillscheid, Federal Republic of Germany indicated between 180 and 190 flowers per plant for May through September observation period.

G. Durability: Medium resistance to rain.

H. Seed production: Fislu has slow fertility; practically no seed is set after pollination.

PLANT

A. Foliage:

*Form.*—Ivy shaped.

*Margin.*—Entire.

*Color (upper surface).*—Approximately 137B.

*Color (zonation).*—No zonation.

*Tolerance of botrytis.*—Good.

B. General appearance and form:

*Internode length.*—3.5–5 cm.

*Branching pattern.*—8.4 after 12 weeks of growing time.

*Height.*—65 cm in August.

I claim:

1. A new and distinct cultivar of geranium plant named Fislu, as illustrated and described.

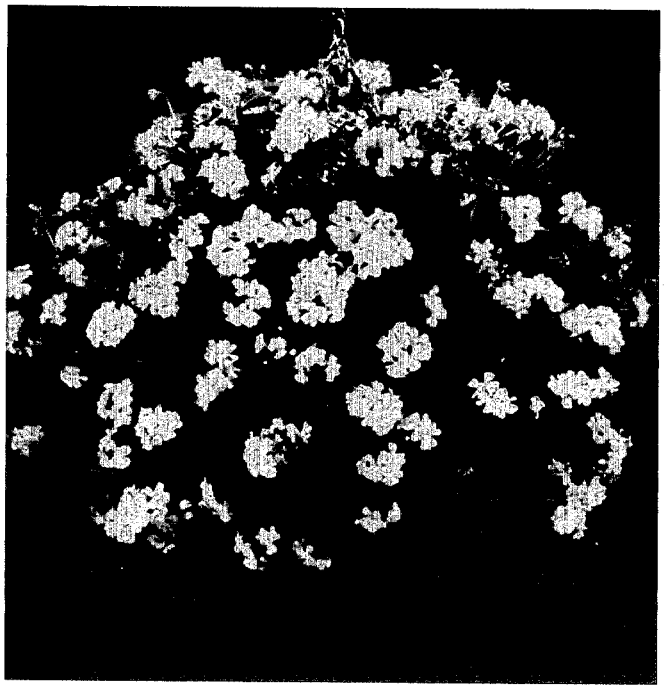

* * * * *